(12) United States Patent
Moorehead

(10) Patent No.: US 6,478,783 B1
(45) Date of Patent: Nov. 12, 2002

(54) ANTI-SLUDGE MEDICATION PORTS AND RELATED METHODS

(76) Inventor: H. Robert Moorehead, 1694 E. 5685 South, Salt Lake City, UT (US) 84121

( * ) Notice: Subject to any disclaimer, the term of this patent is extended or adjusted under 35 U.S.C. 154(b) by 0 days.

(21) Appl. No.: 09/579,944

(22) Filed: May 26, 2000

(51) Int. Cl.$^7$ ............................................. A61M 31/00
(52) U.S. Cl. ........................... 604/288.02; 604/288.04; 604/132
(58) Field of Search ....................... 604/288.01, 288.02, 604/288.03, 288.04, 132, 890.1, 891.1

(56) References Cited

U.S. PATENT DOCUMENTS

| | | | |
|---|---|---|---|
| 3,310,051 A | 3/1967 | Schulte | 128/216 |
| 4,014,328 A | 3/1977 | Cluff et al. | 128/214 |
| 4,400,169 A | 8/1983 | Stephen | 604/49 |
| 4,543,088 A | 9/1985 | Bootman et al. | 604/93 |
| 4,557,722 A | 12/1985 | Harris | 604/9 |
| 4,673,394 A | 6/1987 | Fenton, Jr. et al. | 604/175 |
| 4,681,560 A | 7/1987 | Schulte et al. | 604/9 |
| 4,687,468 A | 8/1987 | Gianturco | 604/153 |
| 4,692,146 A | 9/1987 | Hilger | 604/93 |
| 4,704,103 A | 11/1987 | Stober et al. | 604/175 |
| 4,760,837 A | 8/1988 | Petit | 128/1 R |
| 4,772,270 A | 9/1988 | Wiita et al. | 604/175 |
| 4,772,276 A | 9/1988 | Wiita et al. | 604/283 |
| 4,778,452 A | 10/1988 | Moden et al. | 604/93 |
| 4,781,680 A | 11/1988 | Redmond et al. | 604/93 |
| 4,784,646 A | 11/1988 | Feingold | 604/175 |
| 4,802,885 A | 2/1989 | Weeks et al. | 604/93 |
| 4,816,016 A | 3/1989 | Schulte et al. | 604/9 |
| 4,832,054 A | 5/1989 | Bark | 128/899 |
| 4,861,341 A | 8/1989 | Woodburn | 604/175 |
| 4,886,501 A | 12/1989 | Johnston et al. | 604/175 |
| 4,904,241 A | 2/1990 | Bark | 604/93 |
| 5,006,115 A | 4/1991 | McDonald | 604/175 |
| 5,026,344 A | 6/1991 | Dijkstra et al. | 604/93 |
| 5,041,098 A | 8/1991 | Loiterman et al. | 604/175 |
| 5,045,060 A | 9/1991 | Melsky et al. | 604/93 |
| 5,084,015 A | 1/1992 | Moriuchi | 604/96 |
| RE34,037 E | 8/1992 | Inoue et al. | 604/93 |
| 5,137,529 A | 8/1992 | Watson | 604/891.1 |
| 5,167,638 A | 12/1992 | Felix et al. | 604/175 |
| 5,185,003 A | 2/1993 | Brethauer | 604/93 |
| 5,213,574 A | 5/1993 | Tucker | 604/93 |
| 5,263,930 A | 11/1993 | Ensminger | 604/93 |
| 5,290,263 A | 3/1994 | Wigness et al. | 604/247 |
| 5,318,545 A | 6/1994 | Tucker | 604/244 |
| 5,360,407 A | 11/1994 | Leonard | 604/175 |
| 5,387,192 A | 2/1995 | Glantz et al. | 604/93 |
| 5,476,460 A | 12/1995 | Montalvo | 604/891.1 |
| 5,613,945 A | 3/1997 | Cai et al. | 604/93 |
| 5,718,682 A | 2/1998 | Tucker | 604/93 |
| 5,792,104 A | 8/1998 | Speckman et al. | 604/93 |

*Primary Examiner*—Brian L. Casler
*Assistant Examiner*—Mark K. Han

(57) ABSTRACT

Novel ports to be placed within medical patients for dispensing liquid medication and related methods are disclosed, each port comprising an interior variable volume reservoir for receiving and temporarily storing the liquid medication.

30 Claims, 3 Drawing Sheets

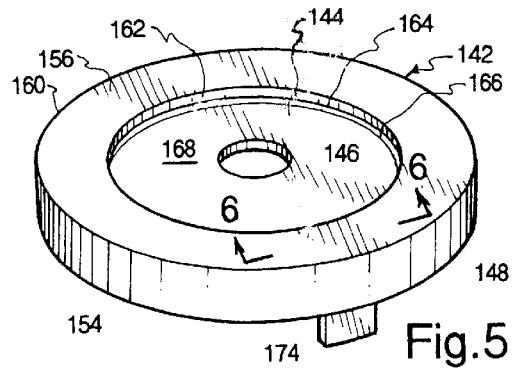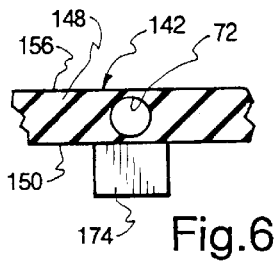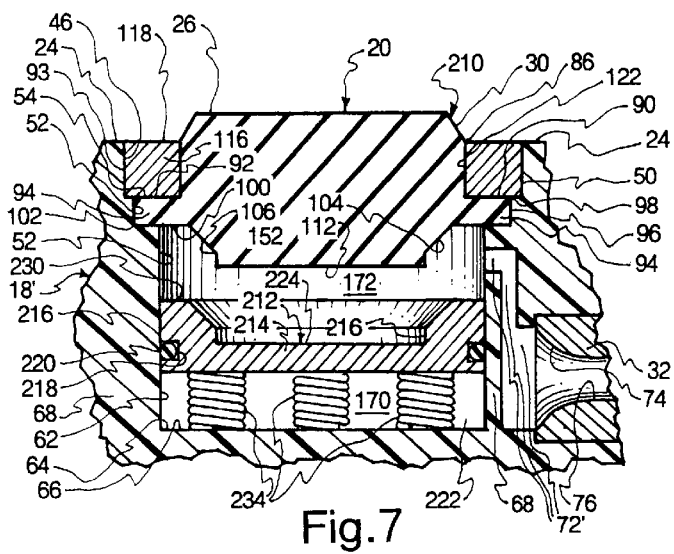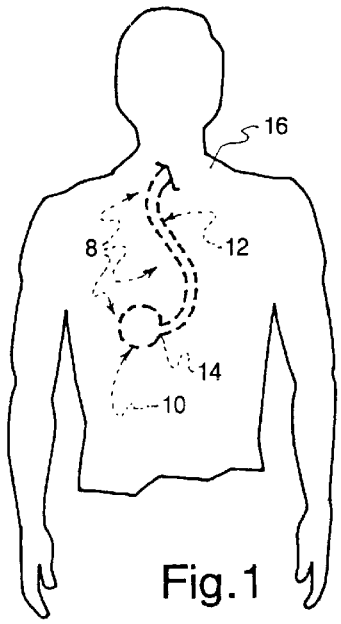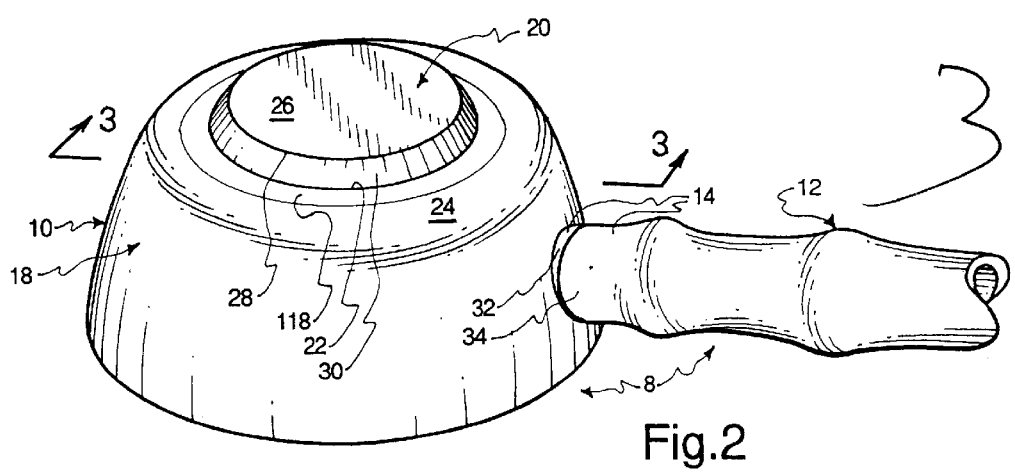

ANTI-SLUDGE MEDICATION PORTS AND RELATED METHODS

FIELD OF THE INVENTION

The present invention relates generally to infusion of liquid medication into a medical patient and, more particularly, to anti-sludge ports and related methods wherein each port is placed indwelling within the patient for delivery of liquid medication to a desired location or site within the patient and/or for blood sampling.

BACKGROUND

Over time, indwelling ports of the prior art develop a thick, ugly sludge from residual liquid retained within the port during the period of use. This creates some risk of displacement of sludge into the patient, creates a problem of potential occlusion of the associated catheter tube and shortens the useful life of the port, requiring premature removal and replacement of the indwelling port.

BRIEF SUMMARY AND OBJECTS OF THE PRESENT INVENTION

In brief summary, the present invention comprises liquid medication dispensing ports, adapted to be placed indwelling within a medical patient, and related methods.

It is a primary object of the present invention to provide novel anti-sludge ports adapted to be placed indwelling within a medical patient for dispensing liquid medication to the patient and/or taking blood samples.

Another primary object is the provision of novel methods by which the build-up of sludge in indwelling medical ports is prevented or substantially alleviated.

These and other objects and features of the present invention will be apparent from the detailed description taken with reference to the accompanying drawings.

BRIEF DESCRIPTION OF THE DRAWINGS

FIG. 1 schematically illustrates a port for dispensing a liquid medication disposed indwelling within a medical patient;

FIG. 2 is a perspective of an anti-sludge port according to the present invention;

FIG. 5 is a perspective of an elastomeric diaphragm comprising a component of the port of FIGS. 2–4;

FIG. 6 is a cross section taken along lines 6—6 of FIG. 5; and

FIG. 7 is a cross section of another anti-sludge port embodiment of the present invention in a position between open and closed positions.

DETAILED DESCRIPTION OF THE ILLUSTRATED EMBODIMENTS

Figure 3:
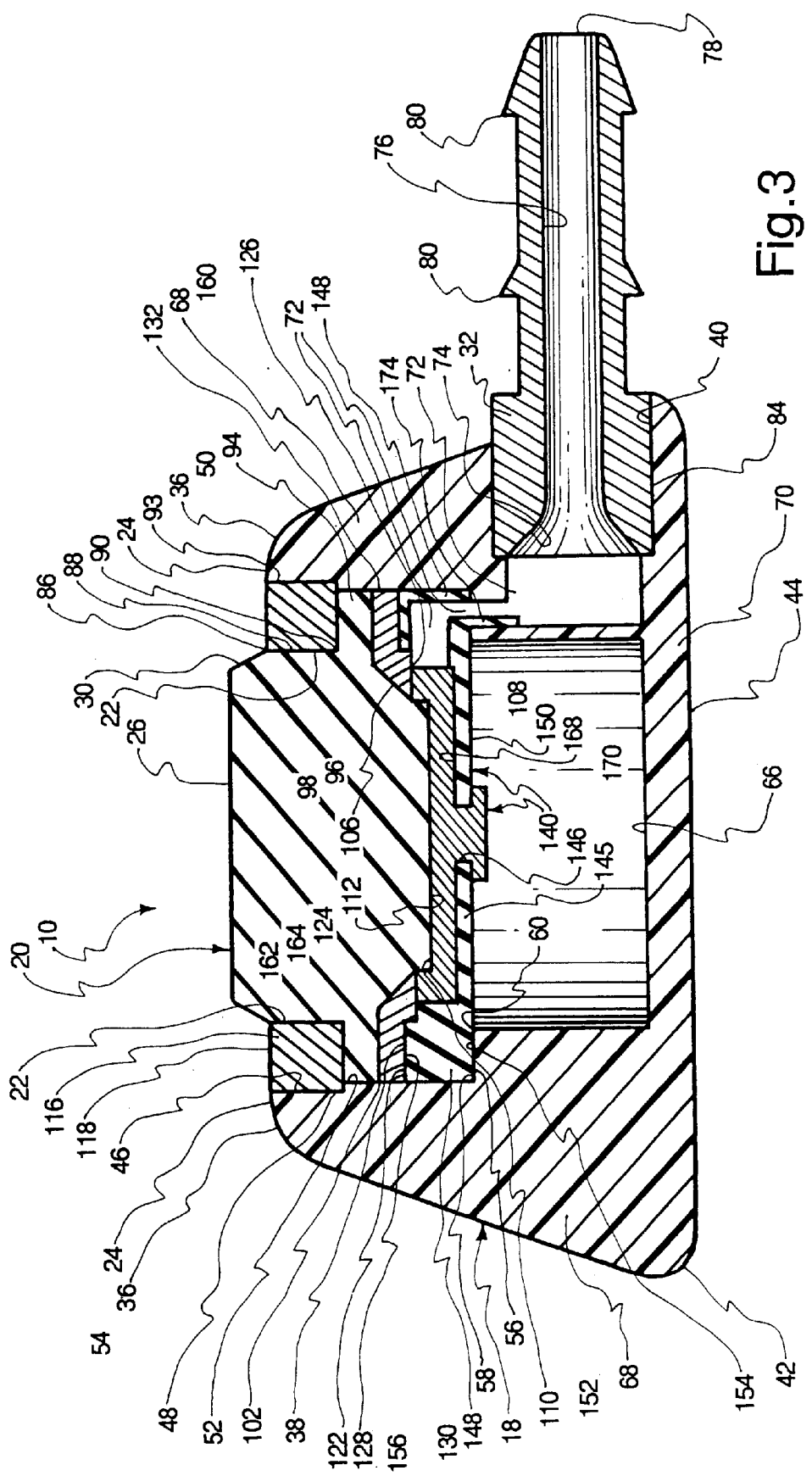
FIG. 3 is a cross section taken along line 3—3 of FIG. 2, showing the anti-sludge port in a closed position.

Reference is now made to the drawings wherein like numerals are used to designate like parts throughout. The present invention is directed toward a port/catheter tube assembly, generally designated 8, shown schematically in its assembled, implanted condition in FIG. 1. The port thereof, generally designated 10, is subcutaneously implanted, typically in the chest region of the patient, with the catheter tube, generally designated 12, connected, at the proximal end thereof, to the port 10 at coupling site 14. The catheter tube 12 may be formed of silicone rubber or other soft, highly flexible synthetic resinous material and is illustrated as comprising a cylindrical wall of uniform thickness throughout defining a hollow interior or passageway 82 within cylindrical wall. As is clear from FIG. 1, the catheter tube is illustrated as being entirely subcutaneously implanted with a distal end of the catheter tube (not shown) being internally disposed at a desired body location, such as a body cavity or an intravascular or intravenous location to which liquid medication is to be selectively directed.

The port/catheter assembly 8 is more appropriate for the patient 16 than is the use of hypodermic injections or intravenous feedings, where the liquid medication being introduced into a specific body site is required over a protracted period of time and typically involves repetitious introduction of the medication over a prolonged period of time. Use of syringe injections does not accommodate a protracted or time-release introduction of the desired medication (such as the chemicals used in chemotherapy)to the desired body site. Use of intravenous feeding equipment or the like inordinately immobilizes the patient, among other things.

The external appearance of port 10, prior to being implanted, may be as shown in FIG. 2. Other external configurations may be used as desired by those skilled in the art. The port 10, shown in FIG. 2, comprises a rigid, shape-retaining, igloo-configurated housing, generally designated 18, and a septum, generally designated 20, placed contiguous, in compression fit relationship, with both an inside surface 22 of a retainer 116 and a surface 46 of the housing 18 essentially flush with top 24 of the housing 18. As illustrated in FIG. 2, septum 20 has an elevation slightly above the top 24 of the housing 18. Septum 20, therefore, comprises an elevated top flat surface 26. Top surface 26 merges at corner 28 with a diagonal surface 30 of the septum.

When subcutaneously implanted, the housing can be readily tactilely located by the nurse or other attendant, under the skin, by use of a finger so that the appropriate injection site for introduction of medication into the port 10 can be readily and accurately located.

The previously mentioned connector 14 between the port 10 and the catheter 12 is illustrated in FIG. 2 as comprising a hollow male stem 32, which is an integral component of the port 10, and the proximal end 34 of the catheter tube 12 compression fit over the hollow stem 32 in such a way, as explained in greater detail hereinafter, so as to prohibit inadvertent separation between the stem 32 and the proximal end 34 of the catheter tube 12.

Figure 4:
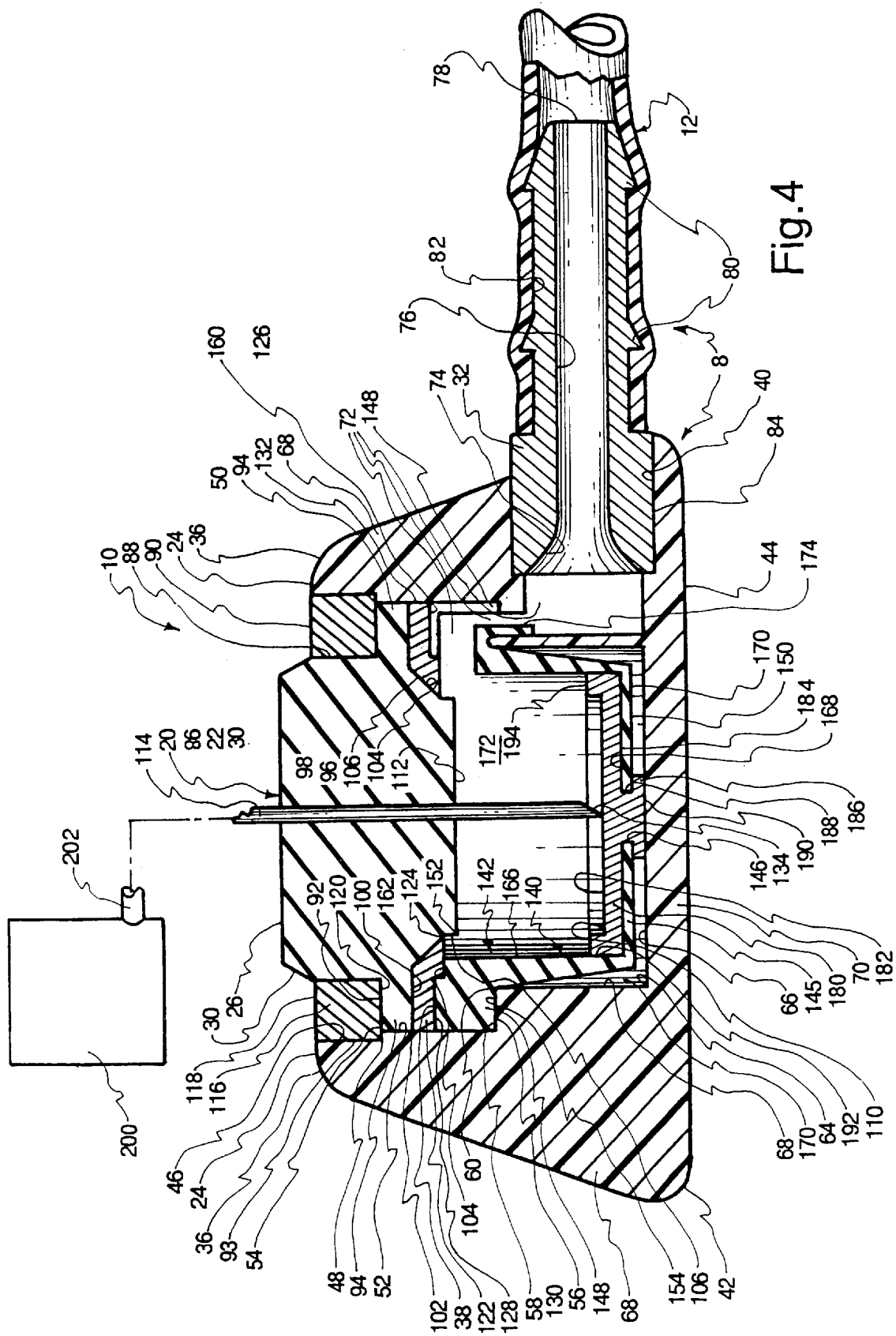
FIG. 4 is a cross section similar to FIG. 3, showing the anti-sludge port in an open position.

The port 10 is illustrated in cross section in FIGS. 3 and 4, FIG. 3 illustrating the closed, anti-sludge position with the catheter tube 12 removed and FIG. 4 illustrating the interior of the port 10 in its fully open position with the catheter tube 12 shown. Port 10 is generally dome-shaped and comprises housing 18 which may be formed from any suitable material, including metal, stainless steel, or implantable grades of thermoplastic, titanium being currently the preference of the industry. More specifically, the housing 18 has a generally frusto-conical configuration, made up of the previously mentioned top surface 24 a top surface transition corner 36, a diagonal side surface 38 interrupted at one location by a cylindrical bore 40, a lower rounded corner surface 42 and a flat base surface 44. The housing 18, in its interior, comprises a stepped blind bore comprising, seriatim, a vertical annular surface 46, which merges at inside corner 48 with an annular inwardly directed horizontal shoulder 50, a vertical annular surface 52, which merges at outside corner 54 with shoulder 50. Surface 52 merges at inside corner 56 with annular shoulder 58. Shoulder 58 merges at outside corner 60 with annular vertical surface 62, which in turn merges at annular inside corner 64 with interior circular base surface 66. Thus, housing 18 comprises essentially an annular vertical wall 68 with a central stepped blind bore formed as one piece with a bottom wall 70.

The interior features of the port 18 described above, are interrupted at side bore 40 in the housing 18 to define a Z-shaped passageway 72, by which liquid medication (placed within the port, as hereinafter more fully described), is dispensed or discharged from the port in a controlled fashion through the hollow interior 76 of the stem 32 and the hollow 82 of the catheter 12 to a desired site within the medical patient 16.

Under normal conditions of use, inadvertent separation of the catheter tube 12 from the port 10 at the coupling site 14 is entirely prevented, safeguarding against toxic introduction of the liquid medication placed from time to time in reservoir 172 into the tissue of the patient and insuring that the medication is properly released at the desired body site in accordance with the treatment indicated for the patient. Thus, the catheter tube is not pulled off the port 10 during movement by the patient and is not blown off by internal pressure which occurs when the reservoir is filled with liquid medication in the manner earlier described.

It is to be appreciated that the connection or coupling at site 14 can be achieved at the factory, if desired. However, the primary aim of the present invention is to accommodate said connection at the time of implantation. If the coupling at site 14 occurs at the factory, then it will be necessary to trim the distal end of the catheter tube during implantation so that the distal end is properly placed at the desired body site. When the coupling at site 14 is accomplished at the time of implantation, which is ordinarily the case, the distal end of the catheter tube is placed in the desired position and the proximal end thereof is trimmed prior to the formation of coupling 14.

Note that the stem 32 comprises a funnel-shaped entry surface at 74, in liquid communication with the Z-shaped passageway 72. Funnel-shaped surface 74 merges with the hollow interior 76 of the stem, the stem 32 terminating at distal end 78.

The exterior of the stem 32 is stepped and comprises one or more barbs 80, which, because of the compression fit, bite into the catheter tube 12 at the interior surface 82 thereof to ensure that the proximal end 34 of the catheter tube 12 does not inadvertently separate from the stem 32.

The exterior surface 84 of the stem 32 is annular and is sized to snugly fit into bore 40 and to be there retained by a compression fit relationship and/or a suitable bonding agent or weld. While the stem 32 is illustrated as being comprised of a metal, such as stainless steel or titanium, it is to be understood that any appropriate material may be used including suitable medical grade synthetic resinous materials.

In respect to the septum 20, top surface 26 merges with annular tapered surface 30, which merges at corner 86 with annular vertical surface 88, which in turn merges at annular inside corner 90 with an annular horizontal surface 92. Surface 92 comprises the top surface of an annular septum flange 94. Annular flange 94 is defined not only by surface 92 but by a vertical annular surface 96, which merges with surface 92 at annular outside corner 98. Similarly, surface 96 merges with lower annular horizontal surface 100 at outside corner 102. Surface 100 is somewhat wider than surface 92 and merges with a diagonal surface 104 at inside corner 106. Similarly, annular diagonal surface 104 merges with annular vertical surface 106 at annular inside corner 108. At annular corner 110, surface 106 merges with a circular base surface 112.

While any suitable elastomeric material may be used to form septum 20, an elastomer comprising silicon rubber is presently preferred because it accommodates penetration by a hollow cannula where the path of penetration by the cannula closes when the cannula is retracted. The cannula may comprise any suitable type, such as a hollow needle 114 as is illustrated in FIG. 4 as having penetrated the septum 20, in a manner and for purposes yet to be explained.

The septum 20 is held in the assembled position illustrated in FIGS. 3 and 4 by a retainer, illustrated as being the nature of retaining ring 116, which is shown as having a rectangular or square cross section with the top surface 118 being flush with the adjacent surface 24 of the housing 18. Retainer ring 116 is preferably compression fit between surfaces 46 and 88, although retention of the ring 116 or other appropriate retainer could be secured by other techniques available to those skilled in the art. The retaining ring 116 comprises a bottom surface 120, which is contiguous with flange surface 92 of the septum 20.

While a suitable metal, such as stainless steel or titanium, may be used to form retainer ring 116, any suitable material may, in the alternative, be used, including appropriate synthetic resinous materials.

An annular skirt 122 is shaped so as to be contiguous at the skirt top with septum surfaces 100 and 104 and comprises an aperture at inwardly directed annular edge 124, which merges with a lower annular surface 126. Surface 126 is stepped downwardly in respect to skirt surface 128, surface 128 being connected to surface 126 across shoulder 130. The perimeter annular surface 132 is contiguous with housing surface 102. The skirt 122 is formed of a material which is impervious to a sharpened distal tip of a cannula, such as tip 134 (shown in FIG. 4) to prevent damage to a yet to be described compartment-forming partition of the port 10. The skirt 122 remains static (in a stationary position) within the port.

As indicated above, the port 10 comprises a movable partition in the nature of a displaceable divider moved from a closed to an open position by physical engagement by a hollow needle and from an open to a closed position by one or more yet to be described return mechanisms as the hollow cannula 114 is retracted. The compartment-forming separator or movable divider is generally designated 140 in FIGS. 3 and 4. FIG. 3 shows the movable partition 140 in its closed position, whereby all of the liquid medication within a liquid chamber, reservoir or compartment of the port is dispensed, extruded or discharged. FIG. 4 illustrates the partition 140 in its fully open position. The movable partition or divider 140 is illustrated as being comprised of two members, i.e., an elastomeric seal and return mechanism, generally designated 142 and a disc-shaped shield or barrier 144 constructed and arranged so as to prevent penetration of the movable partition 140 and particularly penetration of or damage to the elastomeric member 142 by a sharpened point 134 at the distal end of a hollow cannula 114. See FIG. 4. The elastomeric seal and return member 142 comprises a central wall 145, illustrated as being of uniform thickness, in which a central aperture 146 is disposed.

The seal-return-diaphragm member 142, in addition to comprising the central wall portion 145 with the central aperture 146 therein comprises an annular, enlarged peripheral ring 148. Ring 148 merges integrally with central wall section 145 and shares a common flat bottom surface 150. Bottom surface 150 below ring 148 merges with an annular vertical surface 152 at annular inside corner 154. Surface 152 also merges with a top annular horizontal surface 156 at outside corner 160. Upper surface 156 merges with a shoulder 162, which shoulder 162 in turn merges with an upper annular horizontal surface 164. Surface 164 merges with an annular vertical surface 166. Surface 166 merges with the upper surface 168 of the central wall section 145.

The seal-return-diaphragm member 142, in the configuration of FIGS. 3 and 4, must be formed of an elastomeric material having memory, preferably silicon rubber, although other suitable materials could be used. Having a seal implemented by the member 142 is important because the movable partition 140 divides the central interior of the port 10 into two compartments, reservoirs or chambers, i.e., a lower air or other gas compartment or chamber 170 (FIG. 3), which comprises a variable volume chamber, and a higher liquid medication-receiving compartment, chamber or reservoir 172 (FIG. 4).

Simply stated, when the nurse or other medical attendant appropriately desires to introduce a liquid medication into the variable volume reservoir 172, typically and as an example only, a hypodermic needle (with syringe, mechanical pump, drip bottle delivery system or compressible bag attached) is inserted through the septum 20. The attendant next, causes delivery of the liquid medication through the needle into the reservoir 172. This process is repeated from time to time over a prolonged interval so that the long term medication requirements of the patient may be met for the treatment indicated.

It is to be noted that the peripheral ring 148 of the return member 142 is interrupted by the previously mentioned passageway 72. With specific reference to FIGS. 5 and 6, the passageway is defined in part by an interior surface of a thin portion of the peripheral ring 148 and an outside surface of a depending tab 174, as well as circular bore 72.

The impenetrable barrier 144 of the partition 140 may be formed of any suitable material which prohibits penetration by the sharpened tip 134 at the distal end of hollow cannula 114. High molecular rigid synthetic resinous materials may be suitable, as are stainless steel and titanium. Titanium is presently preferred. The barrier 144 comprises a generally flat central layer 180 comprised of a top surface 182 and a bottom surface 184. The bottom surface 184 is interrupted by a central button 186, which comprises a reduced diameter neck portion 188 and an enlarged head 189, which comprises a bottom surface 190, shown as being contiguous with housing surface 66 when the port is in its fully opened position as illustrated in FIG. 4. The diameter of the button head 189 is substantially larger than the unstressed diameter of the aperture 146 in the elastomeric return of member 142. The unstressed diameter at aperture 146 may be essentially the same or somewhat smaller than the diameter of the reduced portion 188 of the button 186. The member 142 is assembled to the barrier member 144 by stretching the member 142 at aperture 146 over the button head 189 so that reduced diameter portion 188 is aligned with aperture 146. As a consequence, the members 142 and 144 are secured together against inadvertent separation by the described entrapment so that together as movable partition they create a seal between compartments 170 and 172 and move collectively between the closed position illustrated in FIG. 3 and the open position illustrated in FIG. 4.

The barrier member 144 comprises a peripheral upwardly directed flange 192 the vertical dimension of which is greater than the vertical dimension of the central portion 180, thereby defining an upwardly extending peripheral shoulder surface 194. Flange 192 is in the nature of an annular ring providing structural reinforcement to the central region 180 and containing the needle against surface 182. In the closed position of FIG. 3, the surface 194 seats against the skirt 122, at surface 126, such that collectively skirt 122 and barrier member 144 are together fully superimposed over elastomeric member 142 in the closed position of FIG. 3 so as to leave no avenue by which the sharpened tip 134 of the hollow cannula 114 could initially reach and penetrate the resilient seal-return member 142.

As the needle 114 is introduced into the port through the septum 20 it is contained within the flange 192 and moves the movable partition 140 from the position of FIG. 3 toward the position of FIG. 4 to provide liquid medication compartment 172 with sufficient volume to accommodate controlled discharge of the liquid medication from the compartment 172 to the patient at a desired location within the patient. When this occurs, the displacement of the movable partition or divider 140 to enlarge the volume of the variable volume compartment 172 and decrease the volumetric size of the variable volume reservoir 170 occurs by force of the needle 114 against the barrier 144 counter to the return memory force of the material from which the elastomeric seal-return member 142 is made.

The return mechanism for the movable partition 140 is not limited to the memory of the material from which member 142 is made but includes also, in the illustrated embodiment but not necessarily as a critical element to the present invention, compressible air or other compressible gas disposed in compartment 170. This compressible gas urges the movable partition 140 from the position of FIG. 4 toward that of FIG. 3. It is to be understood that any suitable return mechanism, including or exclusive of an elastomeric return member and/or compressed air, may be used to urge the movable compartment from its open position toward its closed position.

Once the hollow cannula 114 has placed the movable partition 140 in or nearly in its fully open position as illustrated in FIG. 4, the medical technician will introduce, using conventional equipment, a suitable volume of liquid medication so as to sufficiently fill the compartment 172. For example only, the liquid medication may be contained within a collapsible bag 200 (FIG. 4), which may be equipped with a valve (not shown) by which liquid medication contained within the bag 200 is dispensed along tube 202 under manual pressure and through the hollow of the cannula 114 into the compartment 172, in an essentially conventional manner. It is immaterial to the present invention how the liquid medication is introduced through the hollow of the cannula 114 into the compartment 172.

Also, the exact features of the components of the port illustrated in FIGS. 3 and 4 are not per se critical to the present invention. The nature of the housing and the septum, the manner in which the septum is held in position and the movable partition may be varied in their construction and specifics without departing from the essential nature of the present invention.

Referring again to FIGS. 3 and 4, typically when the port 10 is in the position illustrated in FIG. 3, the hollow interior 76 of the stem 32 and the hollow interior of the catheter 12 are filled with liquid. Accordingly, when the needle 114 displaces the movable partition 140 from the position of FIG. 3 to the position of FIG. 4, a vacuum of modest negative pressure will be created as the compartment 172 is enlarged. This will cause a distal to proximal flow of liquid within the hollow of the catheter 12 and the hollow of the stem 32, but typically of insufficient volume to bring blood from the patient into the compartment 172. Once the compartment 172 is created by placement of the needle, blood withdrawal or infusion of liquid mediation can commence. Conversely, after the prescribed procedure is completed, a flush solution such as a saline solution or a heparinized saline solution will be used to clean the system of residual blood and/or infusate. Note that no residual blood, infusate or flush solution is retained in the compartment 172 after the needle has been removed as the compartment 172 is fully closed.

The port may be reaccessed and used as many times as necessary to complete medical needs of the patient. Indwelling time of the port in the patient can range from days to more than a year.

Once the compartment 172 is fully loaded with liquid medication, that medication is delivered to the patient in whatever predetermined fashion is appropriate for the medical procedure implemented. Typically, the measured amount of liquid medication introduced into the compartment 172 is delivered in its entirety to the patient by fully withdrawing the needle 114 from the septum 20, causing the return mechanism provided by the memory of the material from which member 142 is made and by the compressed gas within compartment 170 to displace the movable partition 140 from the fully open position of FIG. 4 to the closed position of FIG. 3. Note that no residual liquid medication is retained in the compartment 172 as the compartment 172 is fully closed. Accordingly, creation of sludge from blood, residual liquid medication and/or flush solution does not occur in compartment 172 because no material amount of liquid is retained in the port at the end of any medication cycle.

One way of viewing methodology in accordance with the present invention, in respect to substantially preventing build up of sludge in an indwelling port, embraces the acts of a liquid-receiving, variable volume reservoir within the port while the port is indwelling within a medical patient, followed by infusion or introduction of a liquid medication into the reservoir, and thence into the patient and insuring that substantially all liquid medication is extruded, dispensed or discharged from the reservoir by reducing its volumetric size to essentially zero.

Thus, two variable volume compartments, chambers or reservoirs are provided within the port and the volumetric size of one compartment is enlarged while the volumetric size of the other is reduced during operation of the port. Delivery of liquid medication occurs through a septum of the port into one of the compartments and that liquid medication is dispensed to the patient, at a desired location. It should be noted that no reverse flow occurs within the portperse as the cannula or needle is incrementally or completely removed from the port. No blood clotting due to reflux within the port takes place.

Reference is now made to FIG. 7 which illustrates a second port embodiment in accordance with the principles of the present invention. The port embodiment of FIG. 7 is generally designated 210 and comprises several components which are identical or substantially identical to the components of the port 10 illustrated in FIGS. 1–7. These components have been given numerals identical to the numerals used in FIGS. 3 and 4 for the same components and various elements or features of the components, which are depicted in the embodiment of FIG. 7. The housing 18 is illustrated as being comprised of a plastic (although metal could be used) with the wall surface 52' being substantially greater in its vertical dimension than the previously described wall 52. This accommodates deletion of the skirt 122, the return mechanism 142 and the barrier 144.

The passageway 72' is substantially identical to the previously described passageway 72 except a proximal diagonal wall slot 73 is provided to accommodate full discharge of liquid medication from the compartment 172, as hereinafter more fully explained.

The retainer or retaining ring 116 in the embodiment of FIG. 7 is illustrated as being the same or essentially the same as ring 116 in the embodiment of FIGS. 3 and 4.

With the skirt 122 and the movable partition 140 removed, a movable piston, partition or divider, generally designated 212, is provided. Partition 212 comprises a reciprocable piston 214, which is rigid and comprises an annular peripheral surface 216 in which an annular peripheral groove 218 exists. The peripheral groove 218 receives an O-ring 220, which forcibly contiguously engages wall surface 52' so as to create a seal therewith which is maintained as the piston 214 moves up and down.

The piston 214 defines chamber or compartment 172 for receiving liquid medication, in the manner explained above, as well as a second chamber or compartment 170 containing trapped compressible gas which serves, in part, as a return mechanism for displacing the piston 214 in an upward direction, as viewed in FIG. 7, toward a closed position.

The piston 214 comprises a bottom, circular surface 222, which is smooth, and a top recessed surface 224. Surface 224 is configured to contiguously engage septum surface 112 as the piston surfaces 226, 228 and 230 with septum surfaces 106, 104 and 100, respectively, so as to dispense or discharge completely all medication previously infused into the chamber or compartment 172. Note that the surface 230, directly adjacent notch or slot 73, is correspondingly notched or slotted at 232 to provide a flow path for the discharge of all or essentially all of the liquid medication from chamber or compartment 172.

Note also that, as part of the return mechanism for completely placing the piston 214 in its closed position contiguous with the bottom surfaces of the septum 20, three return springs 234 are shown as being provided. While three springs are shown, it is to be appreciated that, consistent with the scope of the present invention, any type of suitable return mechanism could be provided, including, but not necessarily limited to, a single return spring or any plural number of return springs, as would be apparent to one skilled in the art.

It is to be understood that references to horizontal, vertical and similar orientations are in respect to the drawings as set forth in FIGS. 3 and 4 and not to any indwelling orientation of a port according to the present invention implanted within a medical patient or any other orientation.

The invention may be embodied in other specific forms without departing from the spirit of the central characteristics thereof. The present embodiments therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. An anti-sludge port, adapted to be placed indwelling within a medical patient, comprising:
   a housing;
   a variable volume liquid-receiving reservoir within the housing;
   a septum of elastomeric material adapted to be penetrated by a hollow cannula to introduce influent liquid into the variable volume reservoir;
   a retainer securing the septum to the housing;
   a movable partition at least in part defining the variable volume reservoir, the partition being disposed within the housing, biased toward the septum and a closed position which evacuates substantially all liquid from the reservoir and displaceable within the housing counter to the bias to an open position for filling the reservoir with liquid;
   an effluent flow path disposed at least in part within the housing along which the liquid from the reservoir is introduced into the patient.

2. An anti-sludge port according to claim 1 wherein the movable partition is comprised of a barrier which is not penetrated when forcibly engaged by a puncture instrument.

3. An anti-sludge port assembly according to claim 2 wherein the barrier is comprised of metal.

4. An anti-sludge port according to claim 3 wherein the metal comprises titanium.

5. An anti-sludge port according to claim 1 wherein the effluent flow path comprises seriatim a channel within the housing and a hollow stem, the stem being adapted to connect with a proximal end of a catheter tube.

6. An anti-sludge port according to claim 1 wherein the material from which the housing is made is selected from the group consisting of metal and synthetic resinous material.

7. An anti-sludge port according to claim 1 wherein the retainer comprises a retention ring comprised of metal.

8. An anti-sludge port according to claim 1 wherein the movable partition comprises elastomeric material with memory shielded by metal disposed adjacent to the septum.

9. An anti-sludge port, adapted to be placed indwelling within a medical patient, comprising:
   a housing;
   a variable volume liquid-receiving reservoir within the housing;
   a septum of elastomeric material adapted to be penetrated by a hollow cannula to introduce influent liquid into the variable volume reservoir;
   a retainer securing the septum to the housing;
   a movable partition at least in part defining the variable volume reservoir, the partition being disposed within the housing, biased toward the septum and a closed position which evacuates substantially all liquid from the reservoir and displaceable within the housing counter to the bias to an open position for filling the reservoir with liquid;
   the movable partition comprising a central impenetrable barrier having a periphery, the barrier being directly adjacent to the septum and an impenetrable skirt carried by the housing surrounding the periphery of the barrier whereby a hollow cannula penetrating the septum will engage either the barrier or the skirt;
   an effluent flow path disposed at least in part within the housing along which the liquid from the reservoir is introduced into the patient.

10. An anti-sludge port according to claim 9 wherein the movable partition is biased by an elastomeric diaphragm.

11. An anti-sludge port, adapted to be placed indwelling within a medical patient, comprising:
   a housing;
   a variable volume liquid-receiving reservoir within the housing;
   a septum of elastomeric material adapted to be penetrated by a hollow cannula to introduce influent liquid into the variable volume reservoir;
   a retainer securing the septum to the housing;
   a movable partition at least in part defining the variable volume reservoir, the partition being disposed within the housing, biased toward the septum and a closed position which evacuates substantially all liquid from the reservoir and displaceable within the housing counter to the bias to an open position for filling the reservoir with liquid;
   the movable partition comprising an impenetrable barrier adjacent the septum superimposed upon an elastomeric diaphragm with memory, the diaphragm comprising a perimeter secured at the housing and a deflectable region, the memory urging the movable partition toward the closed position;
   an effluent flow path disposed at least in part within the housing along which the liquid from the reservoir is introduced into the patient.

12. An anti-sludge port according to claim 11 wherein the barrier comprises metal and the diaphragm comprises silicon rubber.

13. An anti-sludge port according to claim 11 wherein the barrier and the diaphragm are united.

14. An anti-sludge port according to claim 11 wherein the barrier and the diaphragm are connected, comprising a releasable male/female connector.

15. An anti-sludge port, adapted to be placed indwelling within a medical patient, comprising:
   a housing;
   a variable volume liquid-receiving reservoir within the housing;
   a septum of elastomeric material adapted to be penetrated by a hollow cannula to introduce influent liquid into the variable volume reservoir;
   a retainer securing the septum to the housing;
   a movable partition at least in part defining the variable volume reservoir, the partition being disposed within the housing, biased toward the septum and a closed position which evacuates substantially all liquid from the reservoir and displaceable within the housing counter to the bias to an open position for filling the reservoir with liquid, the bias at least in part being imparted to the movable partition by an elastomeric member comprised of memory and the effluent flow path comprises a port in the elastomeric member;
   an effluent flow path disposed at least in part within the housing along which the liquid from the reservoir is introduced into the patient.

16. An anti-sludge port for placement indwelling within a medical patient comprising, an internal displaceable divider urged by a return mechanism toward a closed position to substantially close a variable volume reservoir within the port, the divider being displaceable counter to the force of the return mechanism from the closed position to an open position to accommodate a material increase in the volume of the reservoir and to accommodate receipt of liquid medication into the reservoir for ultimate delivery from the port to a desired site within the patient.

17. An anti-sludge port for placement indwelling within a medical patient, dual variable volume first and second compartments separated by a movable divider, the first compartment being adapted to store liquid medication for selective delivering from the port to a desired location within the patient and the second compartment comprising a sealed chamber containing a compressible gas which, when compressed, serves to bias the divider in a direction adapted to enlarge the volume of the second compartment and reduce the volume of the first compartment.

18. A method of substantially preventing build-up of sludge in an indwelling port, comprising the acts of:

enlarging the volumetric size of a reservoir within the port while the port is indwelling within a medical patient;

placing a liquid into the reservoir;

displacing the liquid from the reservoir into the patient;

insuring that substantially all of liquid is extruded from the reservoir by reducing the volumetric size of the reservoir to essentially zero.

19. A method according to claim 18 wherein the enlarging act comprises inserting a puncturing instrument through a septum of the port and physically engaging and displacing a wall defining the port with a distal end of the puncturing instrument.

20. A method according to claim 19 wherein the wall comprises a displaceable divider and the displacing act is counter to a bias at or imposed upon the divider.

21. A method according to claim 18 wherein the placing act comprises inserting a hollow cannula through a septum of the port and injecting the liquid medication into the reservoir.

22. A method according to claim 18 wherein the displacing act comprises reducing the volumetric size of the reservoir.

23. A method according to claim 22 wherein the reducing act comprises displacing a wall of the reservoir by a constricting return force while retracting an extending force.

24. A method according to claim 23 wherein the wall displacing act is due at least in part to memory of an elastomeric diaphragm comprising the wall and the extending force is due at least in part to force applied through a hollow needle.

25. A method according to claim 18 wherein the insuring act comprises causing a central partition comprising one wall of the reservoir to mate with a second juxtaposed reservoir wall by at least one return force to extrude substantially all of the liquid medication from variable volume reservoir.

26. A method for preventing build-up of a material amount of sludge in a port indwelling within a medical patient comprising the acts of:

providing two variable volume compartments within the port;

enlarging the volumetric size of one of the compartments, while reducing the volumetric size of the other of the compartments;

delivering liquid through a septum of the port to the one compartment;

displacing liquid from the one compartment into the patient by reducing the volumetric size of the one compartment, while enlarging the volumetric size of the other compartment.

27. A method according to claim 26 wherein the enlarging and reducing acts comprise flexing and deflexing a diaphragm disposed between the two compartments.

28. A method according to claim 26 wherein the enlarging and reducing acts comprise displacing a central barrier disposed between the two compartments by forcibly engaging the cental barrier with a hollow cannula without the cannula penetrating the central barrier.

29. A method according to claim 26 wherein the delivering act comprises infusion of the liquid through a hollow cannula into the one compartment.

30. A method according to claim 26 wherein the displacing act is caused by return mechanism displacement of a wall disposed between the two compartments.

* * * * *